(12) United States Patent
Kikuchi et al.

(10) Patent No.: US 6,531,093 B1
(45) Date of Patent: Mar. 11, 2003

(54) GERMICIDAL CERAMICS, METHOD FOR PRODUCING THE SAME, AND STERILIZING METHOD USING THE SAME

(75) Inventors: Takemitsu Kikuchi, Sendai (JP); Kazutomo Kikuchi, Sendai (JP)

(73) Assignee: Hiromi Houzawa, Iwata-ken (JP)

( * ) Notice: Subject to any disclaimer, the term of this patent is extended or adjusted under 35 U.S.C. 154(b) by 0 days.

(21) Appl. No.: 09/869,068

(22) PCT Filed: Dec. 24, 1998

(86) PCT No.: PCT/JP98/05883

§ 371 (c)(1),
(2), (4) Date: Jun. 22, 2001

(87) PCT Pub. No.: WO00/38526

PCT Pub. Date: Jul. 6, 2000

(51) Int. Cl.[7] .................................................. A61L 9/00
(52) U.S. Cl. ........................................... 422/28; 422/32
(58) Field of Search ............................ 422/1, 5, 28–30, 422/34–37, 261, 292, 905, 906

(56) References Cited

U.S. PATENT DOCUMENTS 4,446,035 A * 5/1984 Barrat et al.
4,986,989 A * 1/1991 Sirosita et al.
5,421,897 A * 6/1995 Grawe
5,541,096 A * 7/1996 Nomura et al.
5,961,843 A * 10/1999 Hayakawa et al.

FOREIGN PATENT DOCUMENTS

JP 08310881 * 11/1996 ............ C04B/38/00
JP 11-029424 2/1999
JP 11-000387 1/2001

OTHER PUBLICATIONS

The food industry, Mori, vol. 41, No. 4, Feb. 28, 1998.*
Mori, vol. 39, No. 1, Jan. 15, 1998.*

* cited by examiner

Primary Examiner—Robert J. Warden, Sr.
Assistant Examiner—Monzer R. Chorbaji
(74) Attorney, Agent, or Firm—Paul A. Guss

(57) ABSTRACT

A germicidal ceramics of an excellent germicidal ability without releasing any substance to damage health of animals and plants, a method for producing the same and a sterilizing method using the same are provided. The germicidal ceramics is produced by mixing zeolite and clamshell in a weight ratio of 90:10 to 50:50 and then pulverizing the both into particles having an average size of not more than 200 $\mu$m. Alternatively, the germicidal ceramics is produced by mixing, in a weight ratio of 90:10 to 50:50, zeolite powder and clamshell powder previously pulverized into the particles having an average size of not more than 200 $\mu$m respectively to prepare mixed powder, then compacting the mixed powder to obtain a compact which is heated at 100 to 300° C. and at 400 to 650° C. in a stepwise manner, and sintering the compact at 700 to 1050° C. The bacteria is sterilized by the germicidal ceramics immersed in a liquid in which the bacteria exist.

8 Claims, 5 Drawing Sheets

| No. | ZEOLITE: CLAMSHELL (WEIGHT RATIO) | LIQUID | pH-ADJUSTING AGENT | pH OF LIQUID UPON START | VIABLE CELL NUMBER | |
|---|---|---|---|---|---|---|
| | | | | | UPON START | AFTER 30 MINUTES |
| EXAMPLE 1 | 67:33 | CONDITIONED WATER | NONE | 10.1 | 3330 | 780 |
| EXAMPLE 2 | | | NaOH | 11.1 | 3330 | 0 |
| EXAMPLE 3 | | DISTILLED WATER | NONE | 10.1 | 3330 | 70 |
| EXAMPLE 4 | | | | 10.3 | 3100 | 0 |
| EXAMPLE 5 | | | | 11.1 | 11700 | 10 |
| EXAMPLE 6 | | | NaOH | 10.7 | 3100 | 0 |
| EXAMPLE 7 | | | | 11.3 | 11700 | 0 |
| EXAMPLE 8 | | | KOH | 11.1 | 3330 | 0 |
| EXAMPLE 9 | 73:27 | CONDITIONED WATER | NONE | 9.4 | 15300 | 7800 |
| EXAMPLE 10 | | | | 10.0 | 8700 | 3700 |
| EXAMPLE 11 | | | NaOH | 10.8 | 15300 | 10 |
| EXAMPLE 12 | | | AQUEOUS NH$_3$ | 11.1 | 8700 | 140 |
| EXAMPLE 13 | | DISTILLED WATER | NONE | 10.0 | 2500 | 410 |
| EXAMPLE 14 | | | | 9.7 | 3170 | 510 |
| EXAMPLE 15 | | | AQUEOUS NH$_3$ | 10.5 | 2500 | 210 |
| EXAMPLE 16 | | | | 10.8 | 3170 | 5 |

FIG. 1

| No. | ZEOLITE: CLAMSHELL (WEIGHT RATIO) | LIQUID | pH-ADJUSTING AGENT | pH OF LIQUID UPON START | VIABLE CELL NUMBER | |
|---|---|---|---|---|---|---|
| | | | | | UPON START | AFTER 30 MINUTES |
| EXAMPLE 1 | 67:33 | CONDITIONED WATER | NONE | 10.1 | 3330 | 780 |
| EXAMPLE 2 | | | NaOH | 11.1 | 3330 | 0 |
| EXAMPLE 3 | | DISTILLED WATER | NONE | 10.1 | 3330 | 70 |
| EXAMPLE 4 | | | | 10.3 | 3100 | 0 |
| EXAMPLE 5 | | | | 11.1 | 11700 | 10 |
| EXAMPLE 6 | | | NaOH | 10.7 | 3100 | 0 |
| EXAMPLE 7 | | | | 11.3 | 11700 | 0 |
| EXAMPLE 8 | | | KOH | 11.1 | 3330 | 0 |
| EXAMPLE 9 | 73:27 | CONDITIONED WATER | NONE | 9.4 | 15300 | 7800 |
| EXAMPLE 10 | | | | 10.0 | 8700 | 3700 |
| EXAMPLE 11 | | | NaOH | 10.8 | 15300 | 10 |
| EXAMPLE 12 | | | AQUEOUS $NH_3$ | 11.1 | 8700 | 140 |
| EXAMPLE 13 | | DISTILLED WATER | NONE | 10.0 | 2500 | 410 |
| EXAMPLE 14 | | | | 9.7 | 3170 | 510 |
| EXAMPLE 15 | | | AQUEOUS $NH_3$ | 10.5 | 2500 | 210 |
| EXAMPLE 16 | | | | 10.8 | 3170 | 5 |

FIG. 2

| No. | ZEOLITE: CLAMSHELL (WEIGHT RATIO) | LIQUID | pH-ADJUSTING AGENT | pH OF LIQUID UPON START | VIABLE CELL NUMBER | |
|---|---|---|---|---|---|---|
| | | | | | UPON START | AFTER 30 MINUTES |
| COMPARATIVE EXAMPLE 1 | 100:0 | CONDITIONED WATER | NONE | 9.2 | 15300 | 30200 |
| COMPARATIVE EXAMPLE 2 | | | NaOH | 11.0 | 15300 | 10400 |
| COMPARATIVE EXAMPLE 3 | | DISTILLED WATER | NONE | 8.4 | 8700 | 800 |
| COMPARATIVE EXAMPLE 4 | | | NaOH | 11.3 | 8700 | 100 |
| COMPARATIVE EXAMPLE 5 | – | CONDITIONED WATER | NaOH | 10.8 | 15300 | 525 |
| COMPARATIVE EXAMPLE 6 | | | | 11.0 | 15300 | 550 |
| COMPARATIVE EXAMPLE 7 | | | AQUEOUS $NH_3$ | 11.1 | 8700 | 420 |
| COMPARATIVE EXAMPLE 8 | | DISTILLED WATER | NaOH | 11.1 | 3330 | 110 |
| COMPARATIVE EXAMPLE 9 | | | | 10.7 | 3100 | 540 |
| COMPARATIVE EXAMPLE 10 | | | | 11.3 | 11700 | 2370 |
| COMPARATIVE EXAMPLE 11 | | | | 11.3 | 8700 | 100 |
| COMPARATIVE EXAMPLE 12 | | | KOH | 11.1 | 3330 | 60 |
| COMPARATIVE EXAMPLE 13 | | | AQUEOUS $NH_3$ | 10.5 | 2500 | 1230 |
| COMPARATIVE EXAMPLE 14 | | | | 10.8 | 3170 | 2550 |

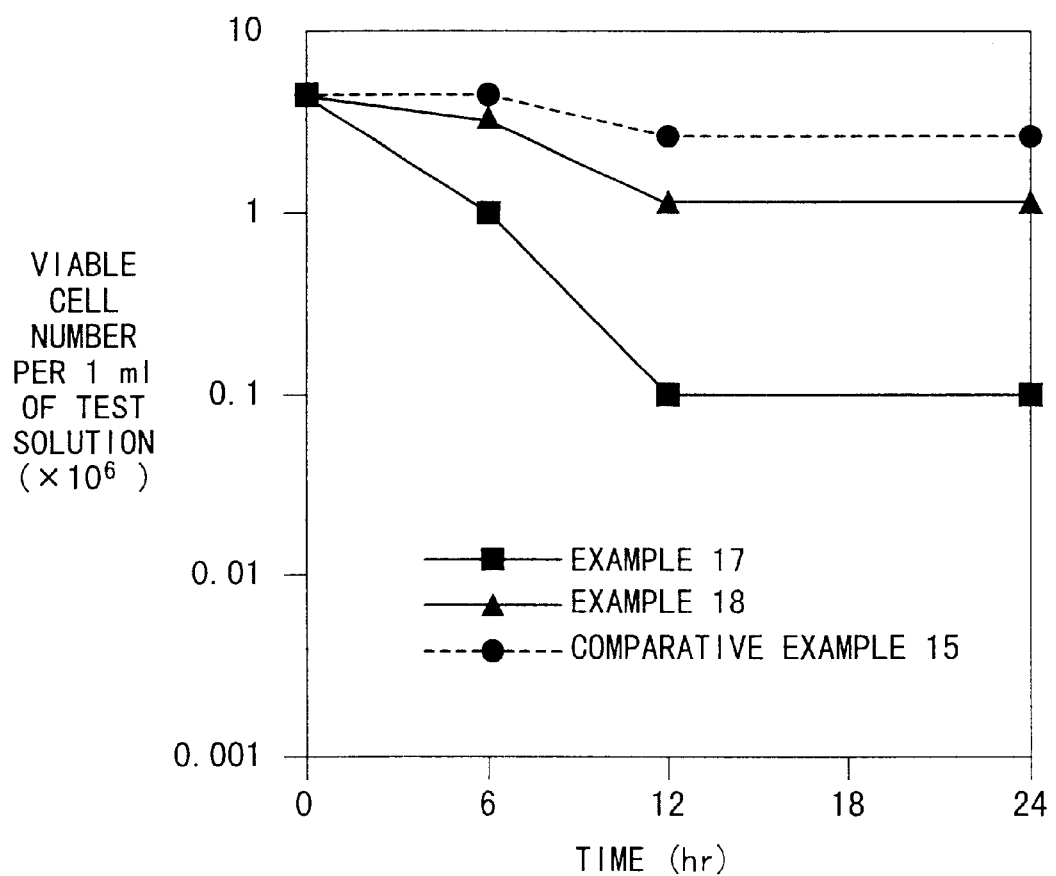

GERMICIDAL CERAMICS, METHOD FOR PRODUCING THE SAME, AND STERILIZING METHOD USING THE SAME

BACKGROUND OF THE INVENTION

1. Field of the Invention

The present invention relates to a germicidal ceramics, a method for producing the same, and a sterilizing method using the same.

2. Description of the Related Art

Generally, water is purified and sterilized before it is supplied to the public as tap water. In the purification process, undesirable impurities are removed from the water. In the sterilization process, sodium hypochlorite is often used as a germicidal agent for killing the remaining bacteria.

However, in recent years, it has been pointed out that the sterilized water is not good for the human health since chlorine liberated from sodium hypochlorite exists in such water.

Chlorine is widely known as a toxic substance. If chlorine of high concentration is ingested by a person, some health problems are likely to occur. For example, the mucous membrane of lungs, nostril or the like is damaged. Even if the chlorine concentration in water is low, assuming that the water is repeatedly ingested by a person for a long period of time, health problems such as arteriosclerosis may occur.

Further, if the liberated chlorine is reacted with an organic matter remaining in tap water, it generates carcinogenic methane trihalide (trihalomethane). It is not favorable for the health to ingest the water containing the carcinogenic substance.

Thus, there is a problem that it is not favorable for the human health to sterilize the tap water with sodium hypochlorite.

Accordingly, it is assumed to solve the above problem by using a substance other than sodium hypochlorite as the germicidal agent.

However, an alternative germicidal agent has not yet been found so far which is excellent in germicidal ability against pathogenic *Escherichia coli* such as O-157 known to cause food poisoning and which is harmless to the human body.

The present invention has been made to solve the above problems. It is an object of the present invention to provide a germicidal ceramics which fast sterilizes bacteria such as *Escherichia coli* without releasing any substance to damage health of animals and plants and to provide a method for producing the same and a sterilizing method using the same.

SUMMARY OF THE INVENTION

The present invention provides a germicidal ceramics comprising 50 to 90 parts by weight of zeolite powder and 50 to 10 parts by weight of clamshell powder, the zeolite powder and the clamshell powder being sintered.

It is another aspect of the present invention to provide a method for producing a germicidal ceramics; comprising a mixing step of mixing zeolite and clamshell in a weight ratio of 90:10 to 50:50 and then pulverizing the both to have an average particle size of not more than 200 $\mu$m, or mixing, in a weight ratio of 90:10 to 50:50, zeolite powder and clamshell powder previously pulverized to have an average particle size of not more than 200 $\mu$m respectively to prepare mixed powder; a compacting step of compacting the mixed powder to prepare a compact; a water-removing step of heating the compact at 100 to 300° C. to remove water from the compact; a subsequent gas/remaining water-removing step of heating the compact at 400 to 650° C. so that carbon dioxide gas can be generated from the clamshell to volatilize and remove the carbon dioxide gas from the compact, and any water remaining in pores of the zeolite is removed; and a heating step of heating the compact at 700 to 1050° C. to sinter the compact so that a sintered compact can be prepared.

It is still another aspect of the present invention to provide a sterilizing method for sterilizing bacteria by immersing, in a liquid in which the bacteria exist, a germicidal ceramics comprising 50 to 90 parts by weight of zeolite powder and 50 to 10 parts by weight of clamshell powder, the zeolite powder and the clamshell powder being sintered.

In the present invention, natural zeolite is preferably used as the zeolite, and at least one of oyster shell and scallop shell is used as the clamshell.

BRIEF DESCRIPTION OF THE DRAWINGS

FIG. 1 shows a table illustrating the germicidal ability of the germicidal ceramics according to an embodiment of the present invention against *Escherichia coli*;

FIG. 2 shows a table illustrating the germicidal ability of the sintered compact obtained by sintering only natural zeolite against *Escherichia coli*, and the change of the viable cell number of *Escherichia coli*, obtained when only the pH-adjusting agent is used;

FIG. 3 shows a graph illustrating the germicidal ability of the germicidal ceramics according to an embodiment of the present invention against Arthrobacter species;

DETAILED DESCRIPTION OF THE PREFERRED EMBODIMENTS

Figure 4:
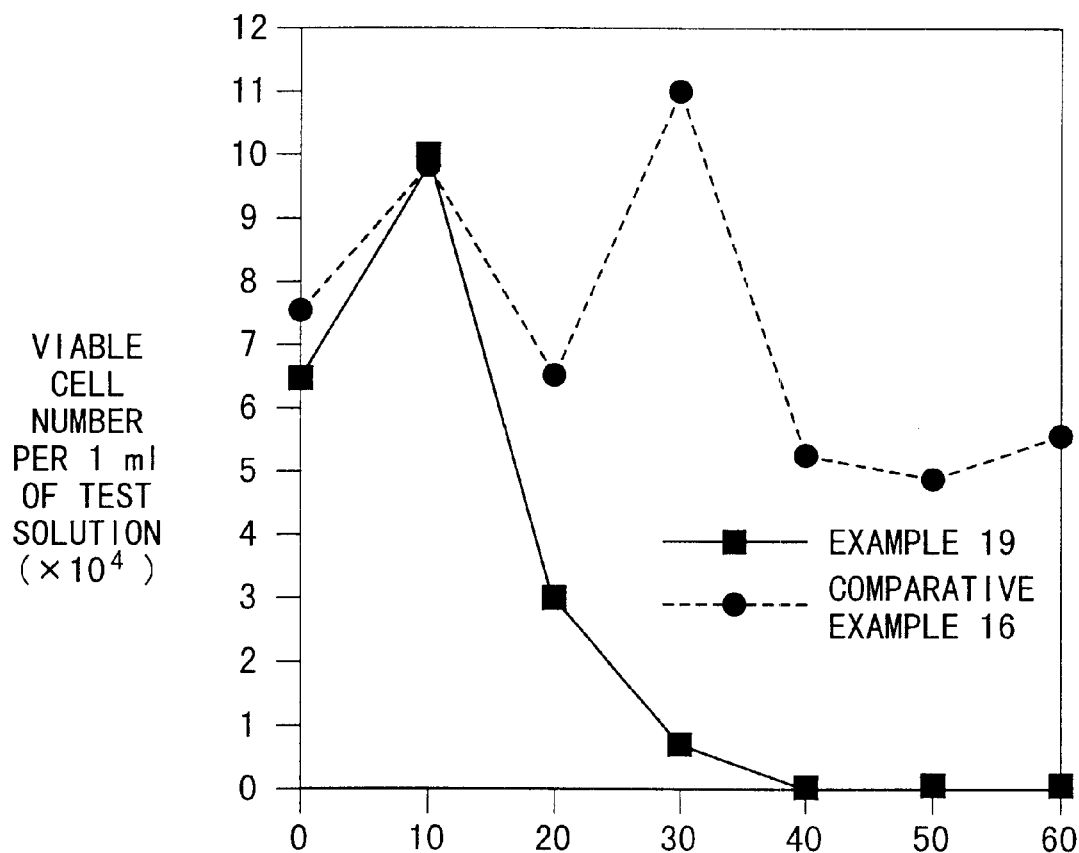
FIG. 4 shows a graph illustrating the germicidal ability of the germicidal ceramics according to an embodiment of the present invention against Legionella species.

A germicidal ceramics, a method for producing the same, and a sterilizing method using the same according to the present invention will be explained in detail below, as exemplified by preferred embodiments.

The germicidal ceramics according to an embodiment the present invention comprises zeolite powder and clamshell powder, the zeolite powder and the clamshell powder being sintered.

Zeolite is a carrier to carry components contained in clamshell. That is, zeolite carries respective components including such as calcium, magnesium, sodium, potassium, lithium, copper, zinc, iron, and manganese contained in the clamshell. These components are released as ions into a liquid when the germicidal ceramics is immersed in the liquid.

Although zeolite is not specifically limited, natural zeolite is preferable in view of its advantageous cost. Mordenite, clinoptilolite or a mixture thereof is specifically preferable in natural zeolite. They can carry a large amount of the above respective components as compared with other natural zeolites. Accordingly, the germicidal ceramics expresses a more excellent germicidal ability if it is obtained by the sintering with them.

The clamshell makes the germicidal ceramics express the germicidal ability.

As described above, the components contained in the clamshell are carried on zeolite. When the germicidal ceramics is immersed in a liquid, the components are released as ions into the liquid. The released ions sterilize the bacteria existing in the liquid. A sintered compact does not express the germicidal ability if it is obtained by sintering only natural zeolite powder or by using calcium carbonate powder as a major component of clamshell in place of the clamshell powder.

Although the clamshell is not specifically limited, oyster shell, scallop shell or the like may be preferably exemplified. The germicidal ceramics produced by using powder of such a material or mixed powder of such materials has the germicidal ability which is much more excellent than that of the germicidal ceramics produced by using powder of other clamshells. Specifically, oyster shell is more preferable since it is excellent in the germicidal ability and is not expensive.

A ratio of weight between zeolite and clamshell in the germicidal ceramics is set to be 50:50 to 90:10. If the weight ratio of clamshell is smaller than 10 parts by weight, the sufficient germicidal ability cannot be obtained. By contrast, if the weight ratio of clamshell is larger than 50 parts by weight, the sintered compact strong enough to be used cannot be obtained.

A method for producing the germicidal ceramics according to an embodiment of the present invention will now be explained.

At first, zeolite and clamshell are mixed. Then, zeolite and clamshell are respectively pulverized into powder and are mixed in a weight ratio of 50:50 to 90:10 so as to obtain mixed powder. Alternatively, after a bulk of zeolite and a bulk of clamshell are mixed in a weight ratio of 50:50 to 90:10, they may be pulverized into mixed powder.

In the pulverization, average particle sizes of the zeolite powder and the clamshell powder are not more than 200 $\mu$m. If the average particle size is larger than 200 $\mu$m, a relative density of the sintered compact is low and a strength thereof is not sufficient.

In this procedure, at least one of zeolite and clamshell is preferably heat-treated in advance before they are mixed. In other words, crystal water contained in zeolite is removed by heat-treating zeolite. Accordingly, it is possible to reduce a time required for the step of removing water from the compact as described later on. When the clamshell is heat-treated, the above respective components contained in clamshell are oxidized and the water with which the clamshell is impregnated is evaporated and removed. Dead bodies of microorganisms or the like adhered to a surface of the clamshell are removed as well.

If clamshell and zeolite are sintered after being heat-treated, the respective components are carried on zeolite easier than those of clamshell and zeolite sintered without the heat treatment. Therefore, the germicidal ability of the germicidal ceramics can be more excellent.

A temperature of heat-treating zeolite and clamshell is 100 to 1000° C. If the heat treatment is performed at a temperature lower than 100° C., it makes the above respective effects poor. If the heat treatment is performed at a temperature higher than 1000° C., it may reduce a carried amount of the components contained in clamshell on zeolite in comparison with a case in which the heat treatment is performed at the temperature of not more than 1000° C. Therefore, the excellent germicidal ability may not be obtained at the temperature higher than 1000° C.

When the heat treatment is applied as described above, zeolite and clamshell are preferably pulverized in advance into particles having an average size of 5 to 10 mm. Zeolite and clamshell thus pulverized are uniformly heat-treated from the surface to the inside. It is difficult to handle the particles having an average size of smaller than 5 mm since, for example, the crystal water in zeolite and the water in clamshell have not removed at this stage and the powder adheres to an inner wall of a mixing machine in the mixing process.

Subsequently, when the mixed powder is compacted into a compact, organic binder or water may be used. Although a shape of the compact is not specifically limited, the preferable shape thereof is spherical because it is easy to be handled. If necessary, the compact may be dried during the compacting process.

Subsequently, the compact is heated at 100 to 300° C. to remove water remaining in the compact. The water is not removed at the temperature lower than 100° C. The compact is cracked in some cases at the temperature higher than 300° C. because carbon dioxide gas starts to vaporize from the compact before the sufficient water is removed.

Subsequently, the compact continues to be heated at the temperature of 400 to 650° C. The carbon dioxide gas generated from the clamshell at this temperature is vaporized and removed out of the compact. The water remaining in pores of zeolite is removed as well.

Finally, the compact is sintered at the temperature of 700 to 1050° C. so as to obtain a sintered compact (germicidal ceramics). The sintering is not advanced at the temperature lower than 700° C. By contrast, if the sintering is performed at the temperature higher than 1050° C., the obtained germicidal ability of the germicidal ceramics is poor in some cases.

The organic binder used in the compacting does not remain in the sintered compact because the organic binder is evaporated, vaporized, and removed during a process of raising and retaining the temperature.

The above respective components contained in clamshell are carried on zeolite in the germicidal ceramics thus obtained. When the germicidal ceramics is immersed in a liquid in which bacteria exist, the respective components are released as ions into the liquid. Consequently, the germicidal ceramics sterilizes the bacteria.

The germicidal ceramics can sterilize, for example, soil bacteria such as Legionella species, *Escherichia coli*, and germs for the inflammation of the intestines. Further, the germicidal ceramics can also sterilize pathogenic *Escherichia coli* such as O-157.

A method for using the germicidal ceramics will now be explained in detail.

The germicidal ceramics sterilizes the bacteria if it contacts with a liquid in which the bacteria exist. In other words, if the germicidal ceramics is immersed in a liquid in which bacteria exist, the bacteria in the liquid are sterilized. For example, if the germicidal ceramics is immersed in well water or in water before being sterilized with sodium hypochlorite, a number of living bacteria such as *Escherichia coli* existing in the water (hereinafter referred to as "viable cell number") is greatly decreased.

If the bacteria existing in food is sterilized, both of the food and the germicidal ceramics may be immersed in water.

In this procedure, a pH-adjusting agent is added to adjust pH of the liquid to be not less than 10.5 after the germicidal ceramics is immersed. The germicidal effect is improved by adding the pH-adjusting agent as compared with a case in which only the germicidal ceramics is immersed. If pH is smaller than 10.5, the germicidal effect is not improved so much.

If a pH range indicates the strong alkalinity, the water or the food in the water which is neutralized with acid may be ingested by animals and plants.

If the animals and the plants ingest the liquid, the pH-adjusting agent which does not damage the health is selected. Such a pH-adjusting agent may be preferably exemplified by sodium hydroxide, potassium hydroxide, and aqueous ammonia which are approved as food additives. They may be used either singly or in mixture.

The zeolite and the heat-treated clamshell are approved as food additives. When the above germicidal ceramics is immersed for a long period of time in tap water from which liberated chlorine is removed, the water satisfies the standard reference for mineral water of Notification No. 393 of the Ministry of Health and Welfare based on the food sanitation law. That is, the above germicidal ceramics does not release any substance which damages the health of the animals and the plants.

The germicidal ability of the germicidal ceramics according to the embodiment of the present invention against several bacteria will now be explained.

At first, the germicidal ability against K-12 which is one species of *Escherichia coli* will be explained.

Natural zeolite was pulverized into 10 mm and was heat-treated. Next, it was further finely pulverized so as to obtain the powder. Similarly, oyster shell was also pulverized into 10 mm and was heat-treated. Next, it was further finely pulverized so as to obtain the powder. The powder of the natural zeolite and the powder of the oyster shell were mixed in a weight ratio of 67:33. The mixed powder was compacted into a sphere having a diameter of 8 mm in a rotary drum. The compact was heated to increase the temperature in a stepwise manner so that it could be sintered to obtain a germicidal ceramics.

K-12 as one species of *Escherichia coli* was introduced into conditioned water (obtained by removing liberated chlorine from tap water) or distilled water in an amount of 300 cc. The viable cell number per 1 ml was determined thereafter by a colony counting method.

Subsequently, after 100 g of the germicidal ceramics was immersed in the conditioned water or in the distilled water and was left to stand for 30 minutes, it was agitated for 30 minutes. The viable cell number was determined again thereafter by the colony counting method.

The viable cell number was determined by the same procedure as described above except that sodium hydroxide was added after being left to stand for 30 minutes to adjust pH to 10.5 to 11.5 and further being left to stand for 30 minutes. Further, the viable cell number was determined in the same manner as described above by using potassium hydroxide or aqueous ammonia in place of sodium hydroxide.

Further, the viable cell numbers per 1 ml in conditioned water or distilled water before and after the immersion were compared with each other by the same procedure as described above except that the germicidal ceramics having a weight ratio of 73:27 between natural zeolite and oyster shell was used. These experiments were designated as Examples 1 to 16 respectively. Obtained results are shown in FIG. 1.

The viable cell numbers per 1 ml before and after the immersion were compared with each other by the same procedure as that adopted for Examples 1 to 16 except that a sintered compact obtained by sintering only natural zeolite was used. These experiments were designated as Comparative Examples 1 to 4 respectively. Obtained results are shown in FIG. 2.

FIGS. 1 and 2 makes it clear that the sintered compact obtained by sintering only natural zeolite does not have the germicidal ability and the germicidal ability is expressed on the germicidal ceramics obtained by sintering natural zeolite and clamshell.

Further, it is to be understood that the viable cell number of K-12 is greatly reduced by not only immersing the germicidal ceramics but also adding the pH-adjusting agent, for example, by comparing the results in Examples 1 and 2 or in Examples 9 and 11. Especially, it is to be understood that, when sodium hydroxide is used as the pH-adjusting agent, almost all cells of K-12 are sterilized.

On the other hand, only the pH-adjusting agent was added without immersing zeolite to compare the number of viable cells per 1 ml before and after adding the pH-adjusting agent. These experiments were designated as Comparative Examples 5 to 14 respectively. Obtained results are shown in FIG. 2 in combination. For example, when the results in Example 7 and Comparative Example 10 are compared with each other, it is to be understood that the germicidal effect is improved by combining the pH-adjusting agent and the germicidal ceramics.

The germicidal ability against Legionella species or Arthrobacter species as soil bacteria will now be explained.

Cells of Arthrobacter species cultivated in a culture medium were uniformly dispersed in a physiological saline solution and were adjusted so that the viable cell number per 1 ml could be $5 \times 10^6$ to prepare a cell suspension.

Subsequently, 200 g of a germicidal ceramics (natural zeolite: clamshell=73:27) washed with sterilized distilled water was placed and stacked in a beaker having a volume of 500 ml.

Subsequently, the cell suspension was poured into the beaker until the liquid level arrived at the stacking height of the germicidal ceramics. This experiment was designated as Example 17.

The operation was performed in the same manner as in Example 17 except that the cell suspension was poured until the liquid level arrived at twice the stacking height of the germicidal ceramics. This experiment was designated as Example 18.

The preparations of Examples 17 and 18 and the cell suspension stood still at the room temperature to investigate the time-dependent change of the viable cell number. FIG. 3 shows the time-dependent change of the viable cell number per 1 ml in the respective experiments. In FIG. 3, the cell suspension is designated as Comparative Example 15.

According to FIG. 3, it is to be understood that the germicidal ceramics also has the germicidal effect on Arthrobacter species. Especially, it is to be understood that the bacterial cells of not less than 90% are sterilized at 12 hours in Example 17.

On the other hand, cells of Legionella species cultivated in B-CYEα medium were uniformly dispersed in a sterilized purified water and were adjusted so that the viable cell number per 1 ml could be about $10^6$ to prepare a cell suspension. 8 ml of the cell suspension was added to 792 ml of sterilized purified water, which was uniformly dispersed so as to obtain a test solution.

Subsequently, a germicidal ceramics (natural zeolite: clamshell=73:27) which was sterilized and treated with high pressure steam was placed in a stainless steel gauge. The gauge was previously sterilized by heating.

Subsequently, the gauge was gradually introduced into the test solution to completely immerse the germicidal ceramics in the test solution. The test solution was agitated by rotating a magnetic stirrer at a number of revolution of 90 to 100 rpm. The time-dependent change of the viable cell number was investigated in this state. This experiment was designated as Example 19.

A test solution was prepared in the same manner as in Example 19 to investigate the time-dependent change of the viable cell number except that the germicidal ceramics was not immersed. This experiment was designated as Comparative Example 16.

FIG. 4 shows the time-dependent change of the viable cell number per 1 ml in Example 19 and Comparative Example 16.

FIG. 4 makes it clear that the germicidal ceramics has the remarkable germicidal ability against Legionella species.

The germicidal ability against *Vibrio parahaemolyticus* as a germ for the inflammation of the intestines will now be explained.

The time-dependent change of the viable cell number was investigated in the same manner as in Example 19 except that *Vibrio parahaemolyticus* cultivated in NA medium was uniformly dispersed in a sterilized saline solution having a concentration of 3% and was adjusted so that the number of cells per 1 ml could be about $10^6$. This experiment was designated as Example 20. On the other hand, a test solution was prepared in the same manner as in Example 20 to investigate the time-dependent change of the viable cell number except that the germicidal ceramics was not immersed.

This experiment was designated as Comparative Example 17.

Figure 5:
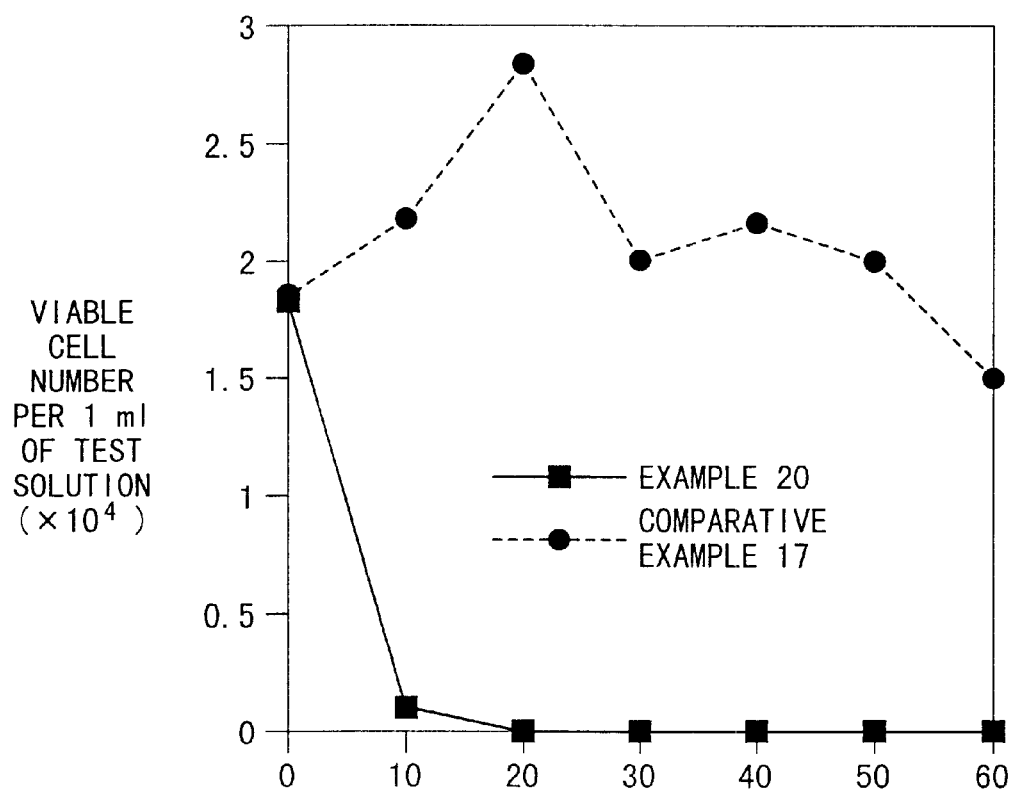
FIG. 5 shows a graph illustrating the germicidal ability of the germicidal ceramics according to an embodiment of the present invention against *Vibrio parahaemolyticus*.

FIG. 5 shows the time-dependent change of the viable cell number per 1 ml in Example 20 and Comparative Example 17 in combination. FIG. 5 makes it clear that the germicidal ceramics also has the remarkable germicidal ability against *Vibrio parahaemolyticus*.

As explained above, the germicidal ceramics of the present invention has the excellent germicidal ability against bacteria such as *Escherichia coli*. Further, the germicidal ceramics does not release any substance which damages the health of the animals and the plants when it is used. Therefore, for example, water for drinking can be sterilized without using sodium hypochlorite.

The method for producing the germicidal ceramics of the present invention makes it possible to efficiently produce the germicidal ceramics durable enough to be used over a long period of time.

The sterilizing method using the germicidal ceramics of the present invention sterilizes the bacteria existing in a liquid by only immersing the germicidal ceramics in the liquid. Accordingly, the bacteria can be sterilized highly conveniently.

What is claimed is:

1. A method for producing germicidal ceramics, comprising:
    a mixing step of mixing zeolite and clamshell in a weight ratio of 90:10 to 50:50 and then pulverizing both into particles having an average size of not more than 200 μm, or mixing, in a weight ratio of 90:10 to 50:50, zeolite powder and clamshell powder previously pulverized into the particles having an average size of not more than 200 μm respectively to prepare a mixed powder;
    a compacting step of compacting said mixed powder to prepare a compact;
    a water-removing step of heating said compact at 100 to 300° C. to partially remove water from said compact;
    a gas and remaining-water-removing step of heating said compact at 400 to 650° C. so that carbon dioxide gas can be generated from said clamshell to volatilize and remove said carbon dioxide gas from said compact, and the water remaining in pores of said zeolite is removed, said gas and remaining-water-removing step being performed subsequently to said water-removing step; and
    a sintering step of heating said compact at 700 to 1050° C. to sinter said compact into a sintered compact, said sintering step being performed subsequently to said gas and remaining-water-removing step.

2. The method for producing said germicidal ceramics according to claim 1, further comprising performing, before said mixing step, a zeolite heat treatment step of heating said zeolite at 100 to 1000° C. to remove crystal water in said zeolite.

3. The method for producing said germicidal ceramics according to claim 2, further comprising performing a zeolite-pre-pulverizing step of pulverizing said zeolite into the particles having a size of 5 to 10 mm before said zeolite heat treatment step.

4. The method for producing said germicidal ceramics according to claim 1, further comprising performing, before said mixing step, a clamshell heat treatment step of heating said clamshell at 100 to 1000° C. to oxidize components contained in said clamshell and remove the water with which said clamshell is impregnated.

5. The method for producing said germicidal ceramics according to claim 4, further comprising performing a clamshell-pre-pulverizing step of pulverizing said clamshell into the particles having a size of 5 to 10 mm before said clamshell heat treatment step.

6. The method for producing said germicidal ceramics according to claim 1, further comprising performing, before said mixing step, a zeolite heat treatment step of heating said zeolite at 100 to 1000° C. to remove crystal water in said zeolite, and a clamshell heat treatment step of heating said clamshell at 100 to 1000° C. to oxidize components contained in said clamshell and remove the water with which said clamshell is impregnated.

7. The method for producing said germicidal ceramics according to claim 6, further comprising performing a zeolite-pre-pulverizing step of pulverizing said zeolite into the particles having a size of 5 to 10 mm before said zeolite heat treatment step, and a clamshell-pre-pulverizing step of pulverizing said clamshell into the particles having a size of 5 to 10 mm before said clamshell heat treatment step.

8. A sterilizing method for sterilizing bacteria by immersing, in a liquid in which said bacteria exist, a germicidal ceramics comprising 50 to 90 parts by weight of zeolite powder and 50 to 10 parts by weight of clamshell powder, said zeolite powder and said clamshell powder being sintered, wherein a pH-adjusting agent selected from one of sodium hydroxide, potassium hydroxide and aqueous ammonia, is added to said liquid so that the pH of said liquid is not less than 10.5 after said germicidal ceramics has been immersed.

* * * * *

UNITED STATES PATENT AND TRADEMARK OFFICE
CERTIFICATE OF CORRECTION

PATENT NO. : 6,531,093 B1
DATED : March 11, 2003
INVENTOR(S) : Takemitsu Kikuchi et al.

It is certified that error appears in the above-identified patent and that said Letters Patent is hereby corrected as shown below:

Title page,
Item [54], Title, correct as follows:
-- METHOD FOR PRODUCING GERMICIDAL CERAMICS AND STERILIZING METHOD USING THE SAME --
Item [73], correct as follows:
-- Assignee: Hiromi Houzawa, Iwate-ken (JP) --

Signed and Sealed this

Twenty-fourth Day of June, 2003

JAMES E. ROGAN
*Director of the United States Patent and Trademark Office*